US 6,664,289 B2

(12) United States Patent
Hansen

(10) Patent No.: US 6,664,289 B2
(45) Date of Patent: Dec. 16, 2003

(54) NASAL SOLUTION CONTAINING A BROAD SPECTRUM MICROBICIDE AND A METHOD FOR ITS USE

(76) Inventor: Richard L. Hansen, 9607 Troy Ct., Mentor, OH (US) 44060

( * ) Notice: Subject to any disclaimer, the term of this patent is extended or adjusted under 35 U.S.C. 154(b) by 0 days.

(21) Appl. No.: 10/139,522

(22) Filed: May 6, 2002

(65) Prior Publication Data

US 2003/0175213 A1 Sep. 18, 2003

Related U.S. Application Data

(60) Provisional application No. 60/365,650, filed on Mar. 18, 2002.

(51) Int. Cl.[7] ................. A61K 31/315; A61K 31/19; A61K 31/045; A61K 33/32; A61K 33/14
(52) U.S. Cl. ................. 514/494; 514/557; 514/738; 424/641; 424/661; 424/663
(58) Field of Search ................. 424/641, 661, 424/663; 514/494, 557, 738

(56) References Cited

U.S. PATENT DOCUMENTS

| | | | |
|---|---|---|---|
| 1,802,662 A | 4/1931 | McKee | |
| 2,739,922 A | 3/1956 | Shelanski | |
| 3,028,300 A | 3/1962 | Cantor et al. | |
| 4,197,318 A | 4/1980 | Sipos | |
| 4,321,257 A | 3/1982 | Sipos | |
| 4,355,021 A | 10/1982 | Mahl et al. | |
| 4,401,651 A | 8/1983 | Knutson | |
| 4,474,748 A | 10/1984 | Sipos | |
| 4,985,234 A | 1/1991 | Nakamura et al. | |
| 5,051,256 A | 9/1991 | Barnes | |
| 5,256,701 A | 10/1993 | Tamura et al. | |
| 5,885,620 A | 3/1999 | Foret | |
| 5,897,872 A | 4/1999 | Picciano | |
| 6,156,293 A | 12/2000 | Jutila et al. | |

*Primary Examiner*—Alton N Pryor
(74) *Attorney, Agent, or Firm*—Laura F. Shunk; Hudak, Shunk & Farine Co. LPA

(57) ABSTRACT

The invention provides for a nasal spray which is an aqueous solution containing a broad spectrum microbicide which may be applied in nasal passages in the manner of a decongestant type nose spray in the event of known or suspected exposure of the individual to common cold virus, flu, or other infective microbial agents. The solution contains active agents which are based on a chlorine or hypochlorite solution, or a solution of chlorine or hypochlorite plus a salt of chloride, bromide or iodide. Alternatively, the solution may contain a bromine solution, or a solution of bromine plus a salt of chloride, bromide or iodide such as sodium chloride, zinc chloride, sodium bromide, zinc bromide, sodium iodide or zinc iodide. The chlorine, hypochlorite, bromine, chloride, bromide, and iodide may originally come from inorganic compounds or organic compounds, which are then dissolved in the water. Further, the solution may contain glycerin or another moisturizing or wetting agent for the nasal mucosa. Zinc gluconate or a zinc halide such as zinc chloride, zinc bromide or zinc iodide may also be included.

25 Claims, No Drawings

NASAL SOLUTION CONTAINING A BROAD SPECTRUM MICROBICIDE AND A METHOD FOR ITS USE

This patent application is based upon U.S. Provisional Application Ser. No. 60/365,650, filed Mar. 18, 2002.

FIELD OF THE INVENTION

The invention relates generally to an aqueous nasal solution for use in treatment of and also the prevention of infection by microbes (like a head cold, flu, or other infection) and generally includes a broad-spectrum microbicide specifically including aqueous chlorine or bromine, hypochlorite ion and/or chloride, bromide or iodide ion.

SUMMARY OF THE INVENTION

The invention relates generally to aqueous solution which contains a broad spectrum microbicide which may be applied in nasal passages in the manner of a decongestant type nose spray. The spray is intended particularly for human use. It is to be applied in the event of known or suspected exposure of the individual to common cold virus, flu, or other infective microbial agents including for example, bacteria, rickettsia, viruses and even mold and fungus. It may also be applied when there is a pre-existing infection caused by the previously mentioned agents. The solution contains an active agent which is based on a chlorine or hypochlorite solution, or a solution of chlorine or hypochlorite plus a salt of chloride, bromide or iodide. Alternatively, the solution may contain a bromine solution, or a solution of bromine plus a salt of chloride, bromide or iodide such as sodium chloride, zinc chloride, sodium bromide, zinc bromide, sodium iodide or zinc iodide. The chlorine, hypochlorite, bromine, chloride, bromide, and iodide may originally come from inorganic compounds or organic compounds, which are then dissolved in the water. Further, the solution may contain glycerin or another moisturizing or wetting agent for the nasal mucosa since the halogens or halides may be dehydrating or drying. Zinc gluconate or a zinc halide such as zinc chloride, zinc bromide or zinc iodide may also be included to further render the nasal mucosa more slippery and thus more difficult for invading microbes to colonize the area.

BACKGROUND OF THE INVENTION

Cold viruses or other microbes are sometimes transmitted by aerosol such as by a water droplet that is dispersed by coughing or sneezing, or by personal contact including, for example, hand to hand contact where a handshake transfers the microbes from one person to another and then the contaminated hand is brought into the vicinity of the individual's nose. (As when touching the nose or scratching it or rubbing it.) It is generally believed that infective agents will grow and multiply in regions where they have the proper temperature, nutrients, and other conditions conducive to growth or multiplication such as in the nasal mucosa. Thus, an object of the present invention is to apply a broad-spectrum microbicide to the area where infective viruses may be transmitted or transported and would ordinarily multiply.

A number of explanations could be proposed for the effectiveness of the microbicide in reducing the risk of full-blown infection. For example, the composition may act to kill the microbe, or to render it ineffective. Further, the microbicide may act to slow diffusion into a cell by tagging it with a heavy ion. This slowing of diffusion may slow the microbe's multiplication and allow the body's natural defenses to catch up and eliminate the microbes. Further, the nasal solution may dilute the attacking organism and wash it out away from the optimum area for growth so as to weaken the statistical probability of success of the infection.

It is thus an object of the invention to apply a medical agent to the area of entry, namely the nose, and specifically the inside of the nose, the nasal fossae and the sinus areas within the nose. This treatment can be remedial so as to inhibit an existing infection, or prophylactic so as to prevent spread into the respiratory system by affecting the microbe in the nose. Thus, in accordance with a method of using the nasal spray, it could be applied as soon as the person has determined he or she has "caught" a cold. It could also be applied after the person first begins to feel the initial symptoms of catching a cold, such as stuffiness or muscular aches or fever. Or it could be applied prophylactically as soon as a person has been exposed to others who have colds and has real reason to be concerned about catching a cold after such an exposure. Moreover, it could be applied in a similar manner for cases of influenza or other infections for minimizing symptoms and extent of "infection".

DETAILED DESCRIPTION OF THE INVENTION

One preferred embodiment of the invention is an aqueous solution of sodium hypochlorite with a halogen salt such as sodium chloride, sodium bromide, sodium iodide, zinc chloride, zinc bromide or zinc iodide. It may also include more than one of the aforementioned salts. In addition, it may also include zinc gluconate.

Another embodiment of the invention would be an aqueous solution of chlorine with a halogen salt such as sodium chloride, sodium bromide, sodium iodide, zinc chloride, zinc bromide or zinc iodide. It may also include more than one of the aforementioned salts. In addition, it may also include zinc gluconate.

Another preferred embodiment of the invention is an aqueous solution of bromine with a halogen salt, i.e. chloride, bromide or iodide. The salt may constitute a chloride, a bromide or iodide with a specific example being sodium bromide, or zinc bromide.

Another embodiment of this invention is the use of organic compounds of chlorine, bromine or iodine, or organic compounds that are chlorides, bromides or iodides. These compounds are such that they decompose in solution or chemically react in order to provide the necessary halogen components for making the aqueous mixture that will be used to spray into the nose onto the nasal mucosa.

There may be particular advantages of using mixed halogens since they sometimes combine in stable but reactive trimers like $Br_2Cl-$, $Br_2I-$, $I_2Cl-$, $I_2Br-$, etc. Having stabilized the reactive halogen, there will likely be more of the halogen present in the solution for reaction with sensitive areas of the microbes existing on the nasal mucosa.

It is postulated that these ionic species will react chemically with organic or biological chemicals on or in the virus so as to kill it or render it ineffective. Further, the solutions can contain glycerin or some other additive to act as a moisturizer since the halogen species tend to have a dehydrating, drying effect on the nasal mucosa. The pH could be adjusted, if necessary, to match the pH of mucous membranes or to optimize the activity without being harmful to the nasal mucosa. It can be adjusted up or down using sodium hydroxide, chlorine, sodium hypochlorite, hydrogen chloride, bromine, or hydrogen bromide. Thus, an appropriate pH for the final solution would be from about pH 5.5 to about pH 8.5, and preferably from about pH 6 to pH 8 and more preferably from about pH 6.5 to pH 7.5.

Sodium hypochlorite would be present in a concentration of about 0.5 ppmw to about 50,000 ppmw, and preferably from about 5 ppmw to about 5000 ppmw and more preferably from about 50 ppmw to 500 ppmw. It may also be potassium, calcium, or other bypochlorites.

Sodium or potassium chloride would be present in a concentration of about 55 ppmw to 75,000 ppmw, and preferably from 250 ppmw to 50,000 ppmw and more preferably from about 2500 ppmw to 25,000 ppmw. This could also be magnesium or calcium chloride or other chlorides.

Sodium or potassium bromide would be present in a concentration of about 0.7 ppmw to about 140,000 ppmw, more preferably from about 140 ppmw to about 55,000 ppmw, and more preferably from about 1,400 ppmw to about 28,000 ppmw. This could also be magnesium or calcium bromide or other bromides.

Sodium or potassium iodide would be present in a concentration of about 0.1 ppmw to about 160,000 ppmw, more preferably from about 200 ppmw to about 80,000 ppmw, and more preferably from about 2,000 ppmw to about 40,000 ppmw.

This could also be magnesium or calcium iodide or other iodides. Chlorine would be present at a concentration of about 0.4 ppmw to about 50,000 ppmw, more preferably from about 2 ppmw to about 5000 ppmw, and more preferably from about 10 ppmw to about 500 ppmw.

Bromine would be present at a concentration of about 1 ppmw to about 75,000 ppmw, more preferably from about 4 ppmw to about 8,000 ppmw, and more preferably from about 20 ppmw to about 1000 ppmw.

Zinc chloride would be present at a concentration of about 0.4 ppmw to about 50,000 ppmw, more preferably from about 40 ppmw to about 15,000 ppmw, and more preferably from about 400 ppmw to about 5,000 ppmw.

Zinc bromide would be present at a concentration of about 0.7 ppmw to about 80,000 ppmw, more preferably from about 75 ppmw to about 33,000 ppmw, and more preferably from about 750 ppmw to about 10,000 ppmw.

Zinc iodide would be present at a concentration of about 1 ppmw to about 120,000 ppmw, more preferably from about 100 ppmw to about 80,000 ppmw, and more preferably from about 1,000 ppmw to about 20,000 ppmw.

Zinc gluconate would be present at a concentration of about 1.7 ppmw to about 60,000 ppmw, more preferably from about 17 ppmw to about 6,000 ppmw, and more preferably from about 170 ppmw to about 1800 ppmw.

Glycerine would be present at a concentration of about 0.01 wt % to about 5 wt %, more preferably from about 0.04 wt % to about 2 wt %, and more preferably from about 0.1 wt % to about 1 wt %. Propylene glycol could be used as a substitute for glycerine.

EXAMPLES

Example 1

An example solution was mixed up and used by a 51 year-old male for the alleviation of head cold symptoms, including the typical nasal congestion. The applications were started early enough in the progress of the cold development that subsequent cold symptoms were relatively minor. It is not known to what extent the treatments altered the total course of the cold development, including its symptoms and extent. In order to provide a more concrete description of the example, the following represents a list in detail of the manner in which the solution was made.

First of all, normal bleach, which is a NaOCl (sodium hypochlorite) solution of strength 5.25%, was obtained. The bleach was chosen to avoid some of the new versions that are marketed that include "lemon freshening", etc. in order to avoid potential side effects from those scenting chemicals. A small quantity of the bleach was diluted to $\frac{1}{5}$th of its original strength by adding 8 drops of the bleach to 32 drops of water to make a total solution of 40 drops of which 8 represent the original bleach. A separate solution was made up by dissolving 1.5 grams of NaI (sodium iodide) crystals in 45 milliliters of water. Once the solute was thoroughly dissolved, then 3 drops of the 1.05% bleach solution were added. The solution was thoroughly mixed and put into a nasal spray bottle.

The spray was administered by spraying 2 to 4 times briskly into the nose while inhaling slightly. This was repeated approximately every 3 to 5 hours as needed. The subject observed a reduction of the mucosa production, as well as a lessening of the irritation of the back of the nose and pharynx, including the tonsils and adenoids. The nose and sinuses continued to decongest with further application of the spray and other cold symptoms were reduced or alleviated.

Example 2

An example solution was mixed up and used by a 45 year-old male for the alleviation of head cold symptoms, including the typical nasal congestion. The applications were started well into the progress of the cold. The subject had been having cold symptoms for nearly a week. It is not known to what extent the treatments altered the total course of the cold development, including its symptoms and extent. In order to provide a more concrete description of the example, the following represents a list in detail of the manner in which the solution was made. First of all, normal bleach, which is a NaOCl (sodium hypochlorite) solution of strength 5.25%, was obtained. The bleach was chosen to avoid some of the new versions that are marketed that include "lemon freshening", etc. in order to avoid potential side effects from those scenting chemicals. A small quantity of the bleach was diluted to $\frac{1}{5}$th of its original strength by adding 8 drops of the bleach to 32 drops of water to make a total solution of 40 drops of which 8 represent the original bleach. A separate solution was made up by dissolving 1.5 grams of NaI (sodium iodide) crystals in 45 milliliters of water. Once the solute was thoroughly dissolved, then 3 drops of the 1.05% bleach solution were added. The solution was thoroughly mixed. Finally, 3 drops of glycerine were added to the solution. The solution was thoroughly mixed and put into a nasal spray bottle.

The spray was administered by spraying 2 to 4 times briskly into the nose while inhaling slightly. This was repeated approximately every 3 to 5 hours as needed. The subject observed a noticeable reduction of the mucosa production, as well as a lessening of the irritation of the back of the nose and pharynx. The nose and sinuses continued to decongest with further application of the spray and other cold symptoms were reduced or alleviated.

Example 3

An example solution was mixed up and used by a 51 year-old male for the alleviation of head cold symptoms, including the typical nasal congestion. The applications were started after about 2 days into the progress of the cold. It is not known to what extent the treatments altered the total course of the cold development, including its symptoms and extent. In order to provide a more concrete description of the example, the following represents a list in detail of the manner in which the solution was made.

First of all, normal bleach, which is a NaOCl (sodium hypochlorite) solution of strength 5.25%, was obtained. The bleach was chosen to avoid some of the new versions that are marketed that include "lemon freshening", etc. in order to avoid potential side effects from those scenting chemicals. A small quantity of the bleach was diluted to ⅕th of its original strength by adding 8 drops of the bleach to 32 drops of water to make a total solution of 40 drops of which 8 represent the original bleach. A separate solution was made up by dissolving 1 gram of NaCl (sodium chloride) crystals in 45 milliliters of water. Once the solute was thoroughly dissolved, then 3 drops of the 1.05% bleach solution were added. The solution was thoroughly mixed. Finally, 3 drops of glycerine were added to the solution. The solution was thoroughly mixed and put into a nasal spray bottle.

The spray was administered by spraying 2 to 4 times briskly into the nose while inhaling slightly. This was repeated approximately every 3 to 5 hours as needed. The subject observed a noticeable reduction of the mucosa production, as well as a lessening of the irritation of the back of the nose and pharynx. The nose and sinuses continued to decongest with further application of the spray and other cold symptoms were reduced or alleviated.

While in accordance with the patent statutes the best mode and preferred embodiment have been set forth, the scope of the invention is not limited thereto, but rather by the scope of the attached claims.

What is claimed is:

1. A method of reducing the risk of microbial infection or of combating a microbial infection which is established first in the nasal mucosa area comprising:

the application of a nasal spray solution within the nose, said nasal spray solution comprising an aqueous solution having the following components:
  a) sodium hypochlorite, potassium hypochlorite, or calcium hypochlorite in a concentration of about 0.5 ppmw to about 50,000 ppmw;
  b) sodium chloride, magnesium chloride, calcium chloride or potassium chloride in a concentration of about 55 ppmw to 75,000 ppmw;
  c) sodium bromide, magnesium bromide, calcium bromide or potassium bromide in a concentration of about 0.7 ppmw to about 140,000 ppmw;
  d) sodium iodide, magnesium iodide, calcium iodide or potassium iodide in a concentration of about 0.1 ppmw to about 160,000 ppmw;
  e) chlorine in a concentration of about 0.4 ppmw to about 50,000 ppmw;
  f) bromine in a concentration of about 1 ppmw to about 75,000 ppmw;
  g) zinc chloride in a concentration of about 0.4 ppmw to about 50,000 ppmw;
  h) zinc bromide in a concentration of about 0.7 ppmw to about 80,000 ppmw; and
  i) zinc iodide in a concentration of about 1 ppmw to about 120,000 ppmw;
  and optionally one or more of zinc gluconate in a concentration of about 1.7 ppmw to about 60,000 ppmw, and glycerine or propylene glycol in a concentration of about 0.01 wt % to about 5 wt %.

2. A method as set forth in claim 1 wherein the concentration of component a) is from about 5 ppmw to about 5,000 ppmw; the concentration of component b) is from about 250 ppmw to about 50,000 ppmw; the concentration of component c) is from about 140 ppmw to about 55,000 ppmw; the concentration of component d) is from about 200 ppmw to about 80,000 ppmw; the concentration of component e) is from about 2 ppmw to about 5,000 ppmw; the concentration of component f) is from about 40 ppmw to about 8,000 ppmw; the concentration of component g) is from about 40 ppmw to about 15,000 ppmw; the concentration of component h) is from about 75 ppmw to about 33,000 ppmw; the concentration of component J) is from about 100 ppmw to about 80,000 ppmw.

3. A method as set forth in claim 2 wherein the concentration of component a) is from about 50 ppmw to about 500 ppmw; the concentration of component b) is from about 2,500 ppmw to about 25,000 ppmw; the concentration of component c) is from about 1,400 ppmw to about 28,000 ppmw; the concentration of component d) is from about 2,000 ppmw to about 40,000 ppmw; the concentration of component e) is from about 10 ppmw to about 500 ppmw; the concentration of component f) is from about 20 ppmw to about 1,000 ppmw; the concentration of component g) is from about 400 ppmw to about 5,000 ppmw; the concentration of component h) is from about 750 ppmw to about 10,000 ppmw; the concentration of component i) is from about 1,000 ppmw to about 20,000 ppmw.

4. A method of reducing the risk of microbial infection and also of combating an established microbial infection which is established first in the nasal mucosa area comprising the application of a nasal spray solution within the nose, said nasal spray solution comprising an aqueous solution having:
  a) from about 0.1 ppmw to 160,000 ppmw sodium bromide sodium iodide or both sodium bromide and sodium iodide;
  b) from about 55 ppmw to 75,000 ppmw of sodium chloride;
  c) from about 0.5 ppmw to about 50,000 ppmw, of sodium hypochlorite;
  d) from about 0.01 wt % to about 5 wt % of glycerin.

5. A method as set forth in claim 4 wherein the concentration of component a) is from about 140 ppmw to about 80,000 ppmw; the concentration of component b) is from about 250 ppmw to about 75,000 ppmw the concentration of component c) is from about 5 ppmw to about 5000 ppmw; the concentration of component d) is from about 0.04 wt % to 2 wt %.

6. A method as set forth in claim 5 wherein the concentration of component a) is from about 1,400 ppmw to about 40,000 ppmw; the concentration of component b) is from about 2,500 ppmw to about 25,000 ppmw; the concentration of component c) is from about 50 ppmw to about 500 ppmw; the concentration of component d) is from about 0.1 wt % to 0.6 wt %.

7. A method of reducing the risk of microbial infection and of combating a microbial infection which is established first in the nasal mucosa area comprising the application of a nasal spray solution within the nose, said nasal spray solution A comprising an aqueous solution having:
  a) sodium hypochlorite, potassium hypochlorite, or calcium hypochlorite in a concentration of about 0.5 ppmw to about 50,000 ppmw;
  b) sodium chloride, magnesium chloride, calcium chloride or potassium chloride in a concentration of about 55 ppmw to 75,000 ppmw;

c) sodium bromide, magnesium bromide, calcium bromide or potassium bromide in a concentration of about 0.7 ppmw to about 140,000 ppmw;

d) sodium iodide, magnesium iodide, calcium iodide or potassium iodide in a concentration of about 0 1 ppmw to about 160,000 ppmw;

e) chlorine in a concentration of about 0.4 ppmw to about 50,000 ppmw;

f) bromine in a concentration of about 1 ppmw to about 75,000 ppmw;

g) zinc chloride in a concentration of about 0.4 ppmw to about 50,000 ppmw;

h) zinc bromide in a concentration of about 0.7 ppmw to about 80,000 ppmw; and i) zinc iodide in a concentration of about 1 ppmw to about 120,000 ppmw;

and optionally one or more of zinc gluconate in a concentration of about 1.7 ppmw to about 60,000 ppmw, and glycerine or propylene glycol in a concentration of about 0.01 wt % to about 5 wt %.

8. A method as set forth in claim 7 wherein the sodium chloride is present in a concentration of from about 250 ppmw to about 50,000 ppmw and the sodium hypochlorite is present in a concentration of from about 5 to about 5,000 ppmw.

9. A method as set forth in claim 8 wherein the sodium chloride is present in a concentration of from about 2,500 ppmw to about 25,000 ppmw and the sodium hypochlorite is present in a concentration of from about 50 to about 500 ppmw.

10. A method of reducing the risk of microbial infection and of combating a microbial infection which is established first in the nasal mucosa area comprising the application of a nasal spray solution within the nose; said nasal spray solution comprising an aqueous solution having:

from about 0.1 ppmw to about 160,000 ppmw of sodium iodide; and from about 0.5 ppmw to about 50,000 ppmw of sodium hypochlorite.

11. A method as set forth in claim 10 wherein the sodium iodide is present in a concentration of from about 200 ppmw to about 80,000 ppmw.

12. A method as set forth in claim 10 wherein the sodium iodide is present in a concentration of from about 2,000 ppmw to about 40,000 ppmw.

13. A method as set forth in claim 10 wherein the sodium hypochlorite is present in a concentration of from about 5 ppmw to about 5,000 ppmw.

14. A method as set forth in claim 13 wherein the sodium hypochlorite is present in a concentration of from about 50 ppmw to about 500 ppmw.

15. A method of reducing the risk of microbial infection and of combating a microbial infection which is established first in the nasal mucosa area comprising the application of a nasal spray solution within the nose, said nasal spray solution comprising an aqueous solution having:

from about 0.1 ppmw to 160,000 ppmw sodium bromide, sodium iodide, or both sodium bromide and sodium iodide;

from about 55 ppmw to 75,000 ppmw of sodium chloride;

from about 0.5 ppmw to about 50,000 ppmw of sodium hypochlorite;

from about 0.01 wt % to about 5 wt % of glycerin. and from about 1.7 ppmw to about 60,000 ppmw of zinc gluconate or zinc bromide.

16. A method of reducing the risk of microbial infection and of combating a microbial infection which is established first in the nasal mucosa area comprising the application of a nasal spray solution within the nose, said nasal spray solution comprising an aqueous solution having:

from about 0.4 ppmw to about 75,000 ppmw chlorine or bromine;

from about 0.1 ppmw to 160,000 ppmw sodium bromide, sodium iodide, or both sodium bromide and sodium iodide;

from about 55 ppmw to 75,000 ppmw of sodium chloride;

from about 0.01 wt % to about 5 wt % of glycerin.

17. A method as set forth in claim 16 further comprising from about 1.7 ppmw to about 60,000 ppmw of zinc gluconate or zinc bromide.

18. A method of reducing the risk of microbial infection and of combating a microbial infection which is established first in the nasal mucosa area comprising the application of a nasal spray solution within the nose, said nasal spray solution comprising an aqueous solution having:

from about 2 ppmw to about 8,000 ppmw chlorine or bromine;

from about 140 ppmw to 80,000 ppmw sodium bromide, sodium iodide, or both sodium bromide and sodium iodide;

from about 250 ppmw to 50,000 ppmw of sodium chloride;

from about 0.04 wt % to about 2 wt % of glycerin and from about 17 ppmw to about 33,000 ppmw of zinc gluconate or zinc bromide.

19. A nasal spray solution comprising an aqueous solution having the following components:

a) sodium hypochlorite, potassium hypochlorite, or calcium hypochlorite in a concentration of about 0.5 ppmw to about 50,000 ppmw;

b) sodium chloride, magnesium chloride, calcium chloride or potassium chloride in a concentration of about 55 ppmw to 75,000 ppmw;

c) sodium bromide, magnesium bromide, calcium bromide or potassium bromide in a concentration of about 0.7 ppmw to about 140,000 ppmw;

d) sodium iodide, magnesium iodide, calcium iodide or potassium iodide in a concentration of about 0.1 ppmw to about 160,000 ppmw;

e) chlorine in a concentration of about 0.4 ppmw to about 50,000 ppmw;

f) bromine in a concentration of about 1 ppmw to about 75,000 ppmw;

g) zinc chloride in a concentration of about 0.4 ppmw to about 50,000 ppmw;

h) zinc bromide in a concentration of about 0.7 ppmw to about 80,000 ppmw; and i) zinc iodide in a concentration of about 1 ppmw to about 120,000 ppmw;

and optionally one or more of zinc gluconate in a concentration of about 1.7 ppmw to about 60,000 ppmw, and glycerine or propylene glycol in a concentration of about 0.01 wt % to about 5 wt %.

20. A nasal spray solution as set forth in claim 19 wherein the concentration of component a) is from about 5 ppmw to about 5,000 ppmw; the concentration of component b) is from about 250 ppmw to about 50,000 ppmw; the concentration of component c) is from about 140 ppmw to about 55,000 ppmw; the concentration of component d) is from about 200 ppmw to about 80,000 ppmw; the concentration of component e) is from about 2 ppmw to about 5,000 ppmw; the concentration of component d) is from about 40 ppmw to about 8,000 ppmw; the concentration of component g) is from about 40 ppmw to about 15,000 ppmw; the concentration of component h) is from about 75 ppmw to about 33,000 ppmw; the concentration of component i) is from about 100 ppmw to about 80,000 ppmw.

21. A nasal spray solution as set forth in claim 20 wherein the concentration of component a) is from about 50 ppmw to about 500 ppmw; the concentration of component b) is from about 2,500 ppmw to about 25,000 ppmw; the concentration of component c) is from about 1,400 ppmw to about 28,000 ppmw; the concentration of component d) is from about 2,000 ppmw to about 40,000 ppmw; the concentration of component e) is from about 10 ppmw to about 500 ppmw; the concentration of component f) is from about 20 ppmw to about 1,000 ppmw; the concentration of component g) is from about 400 ppmw to about 5,000 ppmw; the concentration of component h) is from about 750 ppmw to about 10,000 ppmw; the concentration of component i) is from about 1,000 ppmw to about 20,000 ppmw.

22. A nasal spray solution comprising an aqueous solution having:
 a) from about 0.1 ppmw to 160,000 ppmw sodium bromide, sodium iodide or both sodium bromide and sodium iodide;
 b) from about 55 ppmw to 75,000 ppmw of sodium chloride;
 c) from about 0.5 ppmw to about 50,000 ppmw of sodium hypochlorite;
 d) from about 0.01 wt % to about 5 wt % of glycerin.

23. A nasal spray solution comprising an aqueous solution having:
 from about 0.4 ppmw to about 75,000 chlorine or bromine;
 from about 0.1 ppmw to 160,000 ppmw sodium bromide, sodium iodide, or both sodium bromide and sodium iodide;
 from about 55 ppmw to 75,000 ppmw of sodium chloride;
 from about 0.01 wt % to about 5 wt % of glycerin.

24. A nasal spray solution comprising an aqueous solution having:
 a) sodium hypochlorite, potassium hypochlorite, or calcium hypochlorite in a concentration of about 0.5 ppmw to about 50,000 ppmw;
 b) sodium chloride, magnesium chloride, calcium chloride or potassium chloride in a concentration of about 55 ppmw to 75,000 ppmw;
 c) sodium bromide, magnesium bromide, calcium bromide or potassium bromide in a concentration of about 0.7 ppmw to about 140,000 A 25 ppmw;
 d) sodium iodide, magnesium iodide, calcium iodide or potassium iodide in a concentration of about 0.1 ppmw to about 160,000 ppmw;
 e) chlorine in a concentration of about 0.4 ppmw to about 50,000 ppmw;
 f) bromine in a concentration of about 1 ppmw to about 75,000 ppmw;
 g) zinc chloride in a concentration of about 0.4 ppmw to about 50,000 ppmw;
 h) zinc bromide in a concentration of about 0.7 ppmw to about 80,000 ppmw; and
 i) zinc iodide in a concentration of about 1 ppmw to about 120,000 ppmw;
  and optionally one or more of zinc gluconate in a concentration of about 1.7 ppmw to about 60,000 ppmw, and glycerine or propylene glycol in a concentration of about 0.01 wt % to about 5 wt %.

25. A nasal spray solution comprising an aqueous solution consisting essentially of:
 from about 0.1 ppmw to about 160,000 ppmw of sodium iodide; and
 from about 0.5 ppmw to about 50,000 ppmw of sodium hypochlorite.

* * * * *